United States Patent
Zentai et al.

(10) Patent No.: US 7,054,410 B2
(45) Date of Patent: May 30, 2006

(54) MULTI ENERGY X-RAY IMAGER

(75) Inventors: George Zentai, Mountain View, CA (US); Larry Partain, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 10/439,350

(22) Filed: May 15, 2003

(65) Prior Publication Data

US 2004/0228436 A1  Nov. 18, 2004

(51) Int. Cl.
*G01N 23/00* (2006.01)

(52) U.S. Cl. .................. 378/19; 378/98.8; 250/370.09

(58) Field of Classification Search ............... 378/19, 378/98.8; 250/370.09, 370.11, 370.13, 370.08
See application file for complete search history.

(56) References Cited

U.S. PATENT DOCUMENTS

| 5,079,426 | A | | 1/1992 | Antonuk et al. | 250/370.09 |
|---|---|---|---|---|---|
| 5,262,649 | A | | 11/1993 | Antonuk et al. | 250/370.09 |
| 5,391,882 | A | * | 2/1995 | Rhiger | 250/370.13 |
| 5,598,004 | A | * | 1/1997 | Powell et al. | 250/370.09 |
| 5,729,021 | A | * | 3/1998 | Brauers et al. | 250/370.09 |
| 6,720,812 | B1 | * | 4/2004 | Tumer et al. | 327/170 |
| 2004/0200974 | A1 | | 10/2004 | Harmon et al. | 250/370.12 |

OTHER PUBLICATIONS

Mah, Dennis et al., "Sensitivity of amorphous salerium to x rays from 40 kVp to 16 MV: Measurements and implications for portal imaging", Am. Assoc. Phys. Med., vol. 4, Apr. 1998, pp. 444-456.

\* cited by examiner

*Primary Examiner*—Courtney Thomas
(74) *Attorney, Agent, or Firm*—Bingham McCutchen LLP

(57) ABSTRACT

An X-ray image acquisition apparatus includes a panel having a first electrode, a second electrode, and a photoconductor secured between said first and second electrodes. The photoconductor has a thickness configured to absorb X-ray radiation at a high energy level. The first and second electrodes are configured to create an electric field for transporting charges created in the photoconductor to a pixel unit, thereby allowing charges to be efficiently collected when low or high energy X-ray radiation is used.

36 Claims, 3 Drawing Sheets

MULTI ENERGY X-RAY IMAGER

FIELD OF THE INVENTION

This invention relates generally to image acquisition and, more specifically, to systems and methods for acquiring an X-ray image.

BACKGROUND

X-ray imaging is widely used in various fields of life. For example, X-ray imaging has been a standard medical diagnostic tool for decades.

A typical X-ray image acquisition apparatus suitable for low energy X-rays includes a phosphor X-ray conversion screen and a photo detector array aligned with each other. The phosphor conversion screen generates optical light photons in response to the X-ray radiation. The optical light photons are transmitted to the photo detector array under the conversion screen. The photo detector array generates electric signals in response to the optical light photons. Electronics circuitry coupled to the photo detector array processes the electric signals and generates images.

A typical high energy X-ray image acquisition apparatus includes a copper screen and a Gadolinium Oxysulfide panel over a photo detector array. The high energy X-ray radiation passes through the copper screen, which absorbs a portion of the X-ray radiation and generates energetic electrons. The electrons pass into the Gadolinium Oxysulfide panel and generate optical light photons. Another portion of the X-ray radiation passes through the copper screen and interacts with Gadolinium Oxysulfide to produce optical light photons. The photo detector array senses the optical light photons and generates electric signals in response thereto.

Depending on the particular medical procedure or application, X-ray radiation at different energy levels may be used. For example, in the field of medical diagnostic procedures, low energy "diagnostic" X-ray images are generally used in diagnostics, and high energy X-rays are generally used for treatment in radiation oncology. High energy X-rays may also be used for imaging that are produced in conjunction with the treatment for better patient alignment and target motion detection during the treatment. The quality of the acquired image depends on the image acquisition procedures and the equipment used.

X-ray images at different energy levels are presently created using different image acquisition apparatuses as described above. Maintaining multiple sets of X-ray image apparatuses may increase the operating and overhead costs for a medical diagnostic facility. It may also affect the efficiency of the facility by increasing the idle time of the apparatuses. These effects are exasperated further for those facilities having relatively small patient bases.

Accordingly, it would be advantageous to have an apparatus that is capable of forming images using X-rays at different energy levels. It would be desirable for the apparatus to be simple, reliable, and capable of being used with an existing X-ray imaging system. It would be of further advantage to be able to optimize the image quality for its intended use.

SUMMARY OF THE INVENTION

An X-ray image acquisition apparatus having an X-ray conversion panel aligned with a detector array is provided. The X-ray conversion panel generates a response, such as electron hole pairs, in response to X-ray radiation at different energy levels. The detector array generates electric signals in response to the charges generated by the X-ray conversion panel.

In accordance with an embodiment of the present invention, the conversion panel includes a first electrode, a second electrode, and a photoconductor secured between the first and second electrodes. By way of non-limiting examples, the photoconductor can be made from Mercuric Iodide ($HgI_2$), Lead Iodide ($PbI_2$), Bismuth Iodide ($BiI_3$), Cesium Iodide (CsI), Cadmium Zinc Telluride (CdZnTe), or equivalents thereof. The photoconductor preferably has a thickness configured for absorbing X-ray radiation at a high energy level. In one embodiment, the photoconductor has a thickness greater than 1.0 millimeter. In another embodiment, the panel includes a build-up layer secured to the first electrode or to the photoconductor. In this case, the photoconductor has a thickness greater than 100 microns. The first electrode may include pixel units (i.e., pixellated). The first and second electrodes are configured to create an electric field for transporting charges created in the photoconductor to the pixel units, thereby allowing efficient collection of the charges when low or high energy X-ray radiation is used.

In accordance with another embodiment of the present invention, a method for creating a X-ray image is provided. The method includes providing a photoconductor having a thickness configured to absorb high energy X-ray radiation, and generating an electric field within said photoconductor. In one embodiment, the method further includes absorbing low energy X-ray radiation using the photoconductor. In another embodiment, the method further includes absorbing high energy X-ray radiation using the photoconductor.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
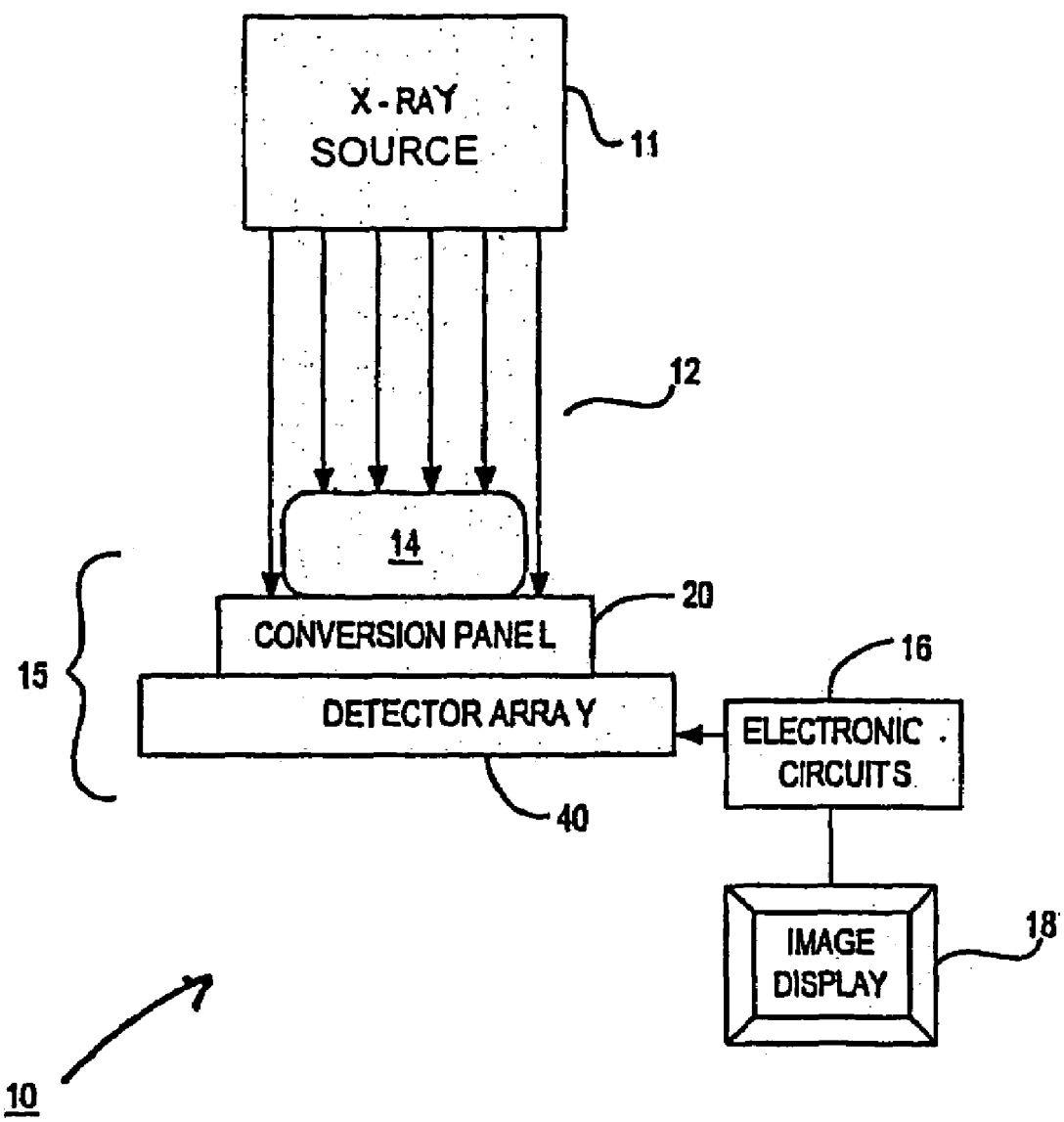
FIG. 1 illustrates an X-ray imaging system that includes an X-ray image acquisition apparatus.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

FIG. 1 is a block diagram schematically illustrating an X-ray imaging system 10 in accordance with an embodiement of the present invention. The X-ray imaging system 10 includes an X-ray source 11 generating X-ray radiation 12 and an X-ray image acquisition apparatus 15. In accordance with a preferred embodiement of the present invention, the radiation source 11 is capable of generating X-ray radiation 12 at various energy levels. By way of example, the radiation source 11 is able to generate X-ray radiation 12 at a plurality of photon energy levels within a range anywhere between approximately 10 kilo-electron-volts (keV) and approximately 20 mega-electron-volts (MeV). Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT" and filed on Nov. 2, 2001, the entirety of which is expressly incorporated herein by reference.

The X-ray radiation 12 is used to form images of an object 14 placed between the radiation source 11 and the X-ray acquisition apparatus 15. The nature of the object 14 depends on the application of the X-ray imaging system 10. For example, in one application in accordance with the present invention, the X-ray imaging system 10 includes a medical diagnostic equipment and the object 14 is a patient. In another application, the X-ray imaging system 10 is a structure inspection equipment and the object 14 is a machine part to be inspected. In yet another application in accordance with the present invention, the X-ray imaging system 10 is a security or custom inspection equipment and object 14 is a piece of luggage or cargo to be inspected. It should be understood that these examples are not meant to be exhaustive regarding the applications of the X-ray imaging system 10.

The X-ray image acquisition apparatus 15 also includes an X-ray conversion panel 20 and a detector array 40 suitably aligned with each other. During an imaging process, the X-ray photons 12 irradiate the X-ray image acquisition apparatus 15. As shown in FIG. 1, portions of the X-ray radiation 12 reaches the X-ray image acquisition apparatus 15 after passing through object 14. Because of their compositions and densities, different parts of the object 14, e.g., different tissues in the body of a patient, may attenuate X-ray radiation 12 differently. For example, the bones in a patient generally attenuate the X-ray radiation 12 more significantly than the soft tissues. In response to X-ray radiation 12 thereon, the X-ray image acquisition apparatus 15 generates electric signals. Electronic circuits 16 coupled to the X-ray image acquisition apparatus 15 processes the electric signals and generates the X-ray images of the object 14 at a display device 18.

Figure 2:
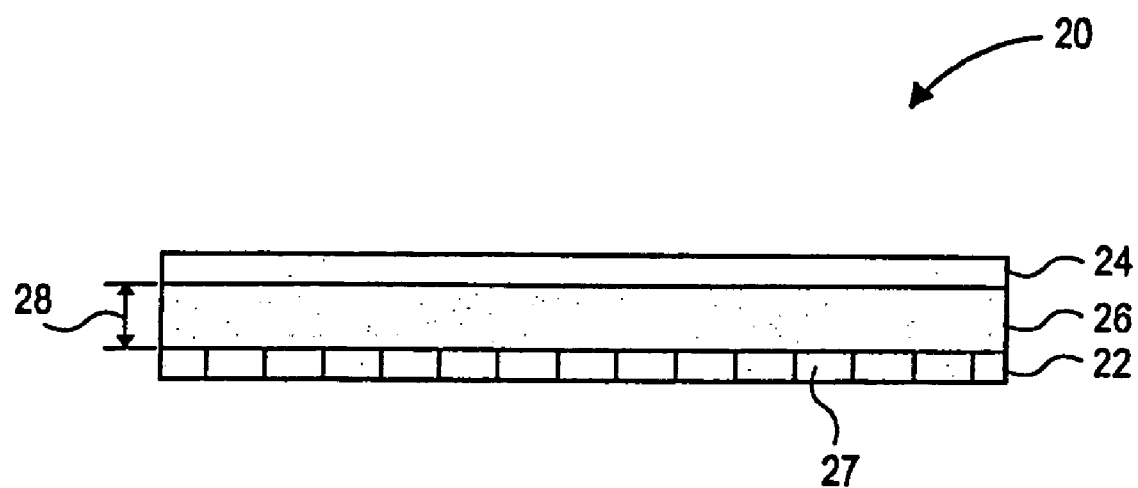
FIG. 2 illustrates a conversion panel in the X-ray image acquisition apparatus of FIG. 1.

FIG. 2 schematically shows the X-ray conversion panel 20 in accordance with an embodiment of the present invention. The panel 20 is configured to generate a response, such as electron hole pairs, in response to the X-ray radiation 12 shown in FIG. 1. As shown in the illustrated embodiment, the panel 20 includes a first electrode 22, a second electrode 24, and a photoconductor 26 secured between the first electrode 22 and the second electrode 24.

Each electrode 22, 24 may be made from a wide variety of materials, such as silver, chromium, aluminum, gold, nickel, vanadium, zinc, palladium, platinum, carbon, etc, and alloys of these materials. Semiconductive layers such as cuprous iodide and indium tin oxide may also be used. In general, materials that are capable of conducting electrical current are suitable for construction of the electrodes 22 and 24. Each electrode 22, 24 may also have a variety of configurations. In a preferred embodiment, the first electrode 22 is pixellated and includes a plurality of pixel units 27, and the second electrode 24 may be pixellated or non-pixellated. Furthermore, each electrode 22, 24 may have a variety of shapes, and is not limited to the planar configuration shown in the illustrated embodiment.

Preferably, the photoconductor 26 is capable of absorbing X-ray radiation at various energy levels. This may be achieved by selecting a suitable material and an appropriate thickness for the conversion photoconductor 26. In one embodiment, the photoconductor 26 is made from a material that comprises a heavy element. Generally, materials having heavy element(s) are preferred for construction of the photoconductor 26 because they are able to better absorb X-ray radiation, and therefore, provide a high X-ray radiation absorption efficiency. As used in this specification, the term "heavy element" refers to element that has an atomic number (Z) greater than 40. Examples of material that can be used includes Mercuric Iodide ($HgI_2$), Lead Iodide ($PbI_2$), Bismuth Iodide ($BiI_3$), Cesium Iodide (CsI), Cadmium Zinc Telluride (CdZnTe), or equivalent thereof. In another embodiment, relatively lighter material (i.e., material that contains an element having an atomic number less than 40), such as Amorphous Selenium (a-Se), may also be used. Other conductive materials known in the art may also be used. The photoconductor 26 may be a single or polycrystalline layer.

Generally, the thicker the photoconductor 26, the more X-ray radiation it can absorb. Preferably, the photoconductor 26 has an optimum thickness depending on X-ray absorption efficiency, image resolution, light collection efficiency, the material(s) used for construction of the photoconductor 26, and other parameters of the X-ray imaging system design. Generally, the heavier the elements within the material used for construction of the photoconductor 26, the thinner the thickness of the photoconductor 26 is required to achieve a given absorption efficiency. The photoconductor 26 preferably has a thickness configured for sufficiently absorbing X-ray radiation at a high energy level. As used in this specification, "high energy" is generally those energies of 160 keV or greater, and more typically 1 MeV or greater, and "low energy" is generally those energies below the high energy range, and more typically below 160 keV. In one embodiment, the photoconductor 26 has a thickness greater than 1.0 millimeter.

Alternatively, the photoconductor 26 may also have a thickness thinner than those described previously if the panel 20 includes a build-up layer. For example, a build-up layer made from copper, tungsten, or gold, may be secured to the first electrode 22, or alternatively be used to substitute the first electrode 22. In this case, the photoconductor 26 can have a thickness greater than about 100 microns. In one embodiment, the build-up layer has a thickness of 1.0 millimeter. However, the build-up layer may also have other thickness, depending on the particular application.

The photoconductor 26 is preferably deposited by physical vapor depositon (PVD) or particle in binder process (PIB). Alternatively, if the photoconductor 26 is deposited on a separate substrate (as it might be the case for CdZnTe), then it may be secured to the first and second electrodes 22 and 24 by indium bump(s). Alternatively, the photoconductor 26 may also be secured to the first and second electrodes 22 and 24 by a suitable adhesive, depending on the materials from which the photoconductor 26 and the first and second electrodes 22 and 24 are made. Other techniques known in the art may also be used to secure the photoconductor 26 to the first and second electrodes 22 and 24.

During use of the X-ray conversion panel 20, the first electrode 22 and the second electrode 24 are biased by a voltage source to create a potential difference or a bias between the first and second electrodes 22 and 24. The voltage source may be, for example, a stabilized power supply. Optionally the bias voltage may change during the x-ray exposure and readout cycle. The biased electrodes 22 and 24 create an electric field across the region between the first and second electrodes 22 and 24. Generally, for a given thickness of the photoconductor 26, the higher the voltage supplied to the electrodes 22 and 24, the higher the electric field created. On the other hand, the thicker the photoconductor 26, the higher the voltage is required to be supplied to the electrodes 22 and 24 in order to create a desired electric field for efficient charge collection.

When the photoconductor 26 is irradiated by high or low energy X-ray, a response, such as electron hole pairs (EHPs) or charges, are generated and drift apart under the influence of the electric field across the region between the first and second electrodes 22 and 24. Charges accelerated by the electric field between the first electrode 22 and the second electrode 24 are collected by the pixel units 27. The charges collected by the pixel units 27 may be negative or positive charges, depending on the polarity of the first and second electrodes 22 and 24.

When high energy X-ray is used, the X-rays are absorbed in the volume of the photoconductor layer. When low energy "diagnostic" X-ray is used, due to the thickness of the photoconductor 26, the X-rays may mostly be absorbed at a top layer of the photoconductor 26. However, because of the electric field created, charges generated can still be accelerated towards a bottom layer of the photoconductor 26 and be collected by the pixel units 27. Furthermore, because the electric field is substantially perpendicular to the surface of the first electrode 22, charges generated are less likely to be scattered to adjacent pixels, resulting in sharper image. As such, the photoconductor 26 may be used in both low energy X-ray system and high energy X-ray system.

Figure 3A:
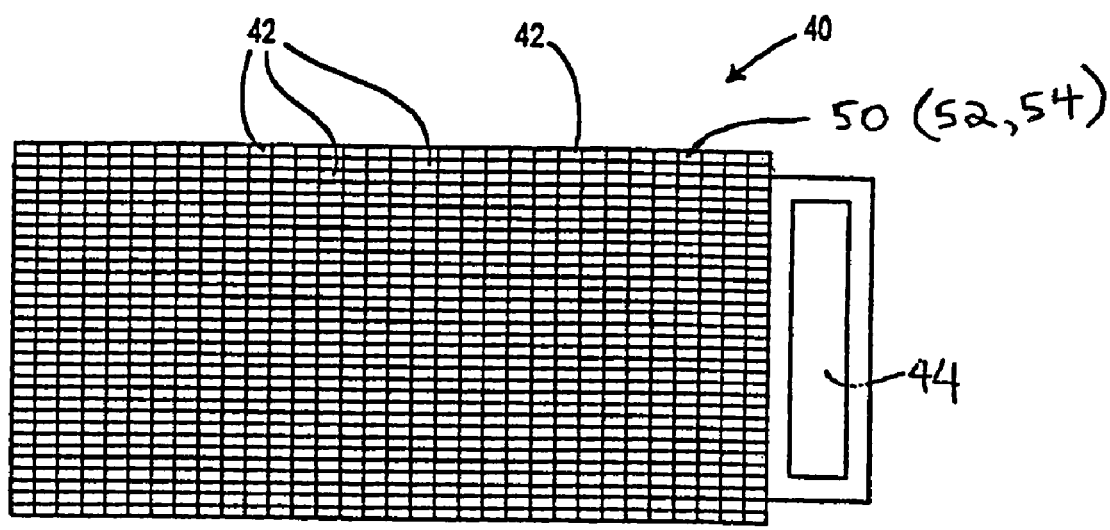
FIGS. 3A and 3B illustrate embodiments of the detector array in the X-ray image acquisition apparatus of FIG. 1.

FIG. 3A is a top view of the detector array 40 of the X-ray image acquisition apparatus 15 in accordance with an embodiment of the present invention. The detector array 40 includes a plurality of detectors 42 arranged in a two-dimensional array. The detectors 42 are configured to generate electric signals in response to the charges collected on the first electrode 22. In a specific embodiment, the detector 42 are amorphous silicon (a-Si:H) charge detectors. Each detector element 42 may have a storage capacitor to store the charge generated by the X-rays and collected by the first electrode 22. Each detector element 42 may also include a switching element 50, such as a thin film transistor (TFT) 52, a switching diode 54, or the like, to access the collected charge by the readout electronics. Optionally the detector elements 42 can contain further components for signal or charge buffering and amplification. The detector 42 may also include polycrystalline silicon or organic active elements. Each of the detectors 42 forms a pixel of the X-ray image generated using the detector array 40. The detector array 40 also includes a pixel access circuit 44 coupled to detectors 42. The pixel access circuit 44 accesses the detectors 42 and reads the electric signals from the detectors 42. The process of accessing detectors 42 and reading electric signals there from is know to those skilled in the art. In accordance with a specific embodiment, pixel access circuit 44 generates row access signals to sequentially access detectors 42 by rows and reads electric signals out of detectors 42 by columns. Each row access signal can access either a signal row or multiple rows of detectors 42. Likewise, each read action can read electric signals from either a signal column or a plurality of columns of the detectors 42.

Figure 3B:
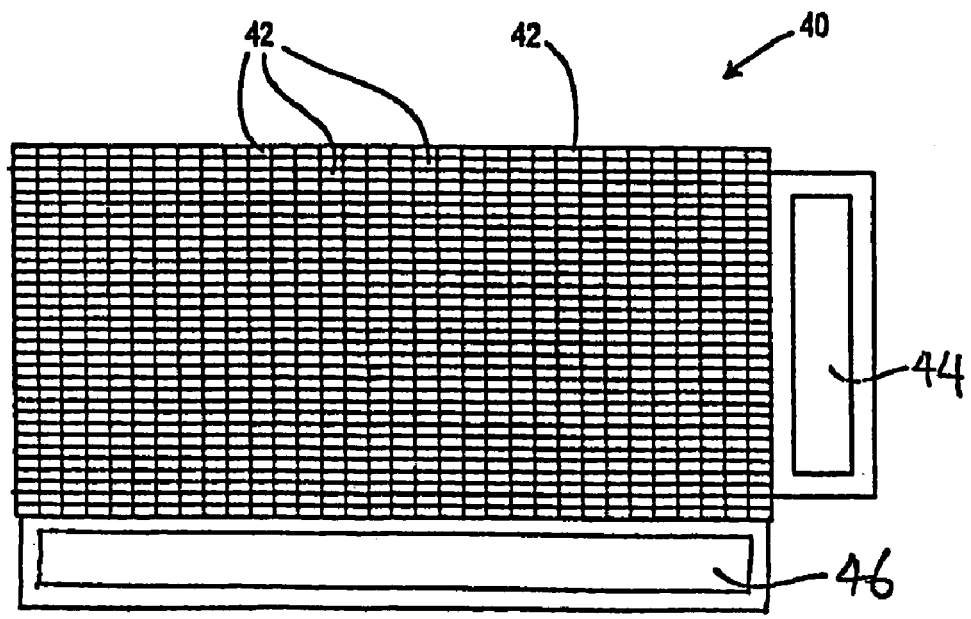

In an alternative embodiment, the detector array 40 may also include an additional pixel access circuit 46 coupled to detectors 42 (FIG. 3B). The pixel access circuit 46 accesses the detectors 42 and reads the electric signals from the detectors 42. In accordance with an embodiment, pixel access circuit 46 generates row access signals to sequentially access detectors 42 by rows and reads electric signals out of detectors 42 by columns. Each row access signal can access either a signal row or multiple rows of detectors 42. In accordance with another embodiment, pixel access circuit 46 generates column access signals to sequentially access detectors 42 by columns and reads electric signals out of detectors 42 by rows. Each column access signal can access either a signal column or multiple columns of detectors 42.

The size of each detector element 42, which is also referred to as a pixel size, determines the maximum theoretical spatial resolution of the X-ray images generated using the detector array 40. Smaller pixel size results in better spatial resolution, in general. Accessing more than one rows and reading electric signals from more than one columns during each read action increase the reading speed, but it will result in lower spatial resolution.

Preferably, the detectors 42 in the detector array 40 are aligned with the pixel units 27 of the first electrodes 22 in the X-ray conversion panel 20. In one embodiment, each pixel unit 27 is aligned with one detector 42 in the detector array 40. In this embodiment, the size of the pixel units 27 is about the same as that of the detectors 42. The maximum spatial resolution of the X-ray images generated using the X-ray image acquisition apparatus 15 is equal to the pixel size of the detectors 42 in the detector array 40. In an alternative embodiment, the pixel units 27 of the first electrodes 22 in the X-ray conversion panel 20 are larger than the detectors 42 in the detector array 40 and each first electrode 22 is aligned with more than one detectors 42. In this embodiment, the maximum spatial resolution of the X-ray images is determined by the size of first electrodes 22.

FIG. 3A shows the pixel access circuit 44 located on the side of the detectors 42. This arrangement keeps the pixel access circuit 44 out of the propagation paths of the X-ray radiation 12 from the X-ray source 11 and the charges generated in the conversion panel 20, thereby benefiting the lifetime of the pixel access circuit 44. However, the present invention is not limited to such an arrangement. In an alternative embodiment, the detectors 42 are mounted on one side of a substrate and the pixel access circuit 44 is located on the other side of the substrate. In this case the detector array 40 also includes the pixel access circuit 44. The substrate protects the pixel access circuit 44 from possible damage caused by the X-ray radiation and the charges generated in the conversion panel 20. This arrangement reduces the physical size of the detector array 40 without reducing the number of pixels therein.

In the above described embodiments, the first electrode 22 has been described as being a part of the conversion panel 20. In an alternative embodiment, the detector array 40 may include the first electrode 22. In this case, the conversion panel 20 would only include the second electrode 24 and the photoconductor 26.

By now it should be appreciated that an X-ray image acquisition apparatus capable of forming images of X-rays at different energy levels has been provided. The X-ray image acquisition apparatus in accordance with the present invention includes an X-ray conversion panel aligned with a detector array. The X-ray conversion panel is configured to generate a response, such as electron hole pairs, in response to X-ray radiation over a wide range of energy levels. The conversion panel includes a first electrode, a second electrode, and a photoconductor secured between the first electrode and the second electrode. The photoconductor is made of a material that efficiently generates a response, such as electron hole pairs, in response to X-ray radiation illuminating thereon. The photoconductor preferably has a thickness configured for absorbing the X-ray radiation at a high energy level. The detector array aligned with the conversion panel is configured to generate electric signals in response to charges received from the conversion panel. Electronic circuits coupled to the detector array process the electric signals and generate the images.

It should be understood that various modifications of the above described embodiments can be made by those skilled in the art after reading the specification of the subject application. These modifications are within the scope of the present invention. For example, the detector array 40 in the X-ray image acquisition apparatus 10 can be replaced with a charge detector that is capable of performing the same functions described herein. Further, the X-ray image acquisition apparatus 10 is not limited to being used on an imaging system with an X-ray radiation source capable of generating X-rays at different energy levels. The X-ray image acquisition apparatus 10 can be used on different imaging systems, each system including an X-ray radiation source that is capable of generating X-ray radiation either at a single energy level or at multiple energy levels.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. An X-ray image acquisition apparatus, comprising:
a panel having a first electrode, a second electrode, and a photoconductor secured between said first and second electrodes, said photoconductor being made from a material that comprises a heavy element, wherein said first and second electrodes create an electric field for transporting charges created in the photoconductor, said photoconductor configured to absorb X-ray radiation at an energy level that is higher than 1000 kilo-electron-volts; and
an array of detector elements adjacent the panel, at least one of the detector elements having a switching element coupled to the second electrode.

2. The X-ray image acquisition apparatus of claim 1, wherein said photoconductor is made from a material selected from the group consisting of Lead Iodide, Cesium Iodide, Mercuric Iodide, Bismuth Iodide, and Cadmium Zinc Telluride.

3. The X-ray image acquisition apparatus of claim 1, wherein said first electrode is pixellated.

4. The X-ray image acquisition apparatus of claim 1, wherein said photoconductor comprises a single crystalline layer.

5. The X-ray image acquisition apparatus of claim 1, wherein said photoconductor comprises a poly-crystalline layer.

6. The X-ray image acquisition apparatus of claim 1, wherein said photoconductor is adapted for absorbing X-ray radiation at a plurality of energy levels within a range between approximately 10 kilo-electron-volts and approximately 20 Mega-electron-volts.

7. The X-ray image acquisition apparatus of claim 1, wherein said photoconductor is adapted for absorbing high X-ray radiation energy and low X-ray radiation energy.

8. The X-ray image acquisition apparatus of claim 1, wherein said first electrode comprises a build-up layer.

9. The X-ray image acquisition apparatus of claim 8, wherein said build-up layer comprises a material selected from the group consisting of copper, tungsten, and gold.

10. The X-ray image acquisition apparatus of claim 8, wherein said photoconductor has a thickness greater than about 100 microns.

11. The X-ray image acquisition apparatus of claim 1, further comprising a build-up layer secured to said first electrode.

12. The X-ray image acquisition apparatus of claim 11, wherein said photoconductor has a thickness greater than about 100 microns.

13. The X-ray image acquisition apparatus of claim 1, wherein said photoconductor has a thickness greater than about 1 mm.

14. The X-ray image acquisition apparatus of claim 1, wherein the switching element comprises a thin film transistor.

15. The X-ray image acquisition apparatus of claim 1, wherein the switching element comprises a switching diode.

16. The X-ray image acquisition apparatus of claim 1, wherein the switching element comprises a polycrystalline silicon.

17. The X-ray image acquisition apparatus of claim 1, wherein the switching element comprises an organic active element.

18. An X-ray image acquisition apparatus, comprising:
a panel having a first electrode, a second electrode, and a photoconductor secured between said first and second electrodes, said photoconductor being made from a material that comprises a heavy element; and
an array of detector elements adjacent the panel, at least one of the detector elements having a switching element coupled to the second electrode;
wherein said first and second electrodes create an electric field for transporting charges created in the photoconductor, said photoconductor having a thickness configured to absorb X-ray radiation at a high energy level, wherein said photoconductor has a thickness greater than 1 mm.

19. The X-ray image acquisition apparatus of claim 18, wherein the high energy level is at least 160 kilo-electron-volts.

20. The X-ray image acquisition apparatus of claim 19, wherein said photoconductor is configured to absorb X-ray radiation at an energy level that is higher than 1000 kilo-electron-volts.

21. The X-ray image acquisition apparatus of claim 18, wherein said photoconductor is adapted for absorbing X-ray radiation at a plurality of energy levels within a range between approximately 10 kilo-electron-volts and approximately 20 Mega-electron-volts.

22. The X-ray image acquisition apparatus of claim 18, wherein said photoconductor is adapted for absorbing high X-ray radiation energy and low X-ray radiation energy.

23. A method for creating a X-ray image, comprising:
providing a photoconductor, said photoconductor having a thickness configured to absorb X-ray radiation at an energy level that is higher than 1000 kilo-electron-volts;
generating an electric field within said photoconductor to thereby transport charges to an electrode; and
using a detector array to access a signal from the electrode, the detector array having at least one switching element.

24. The method of claim 23, further comprising absorbing low energy X-ray radiation using said photoconductor.

25. The method of claim 23, further comprising absorbing high energy X-ray radiation using said photoconductor.

26. The method of claim 23, wherein said generating comprises creating a potential difference between a first electrode located on one side of said photoconductor and a second electrode located on another side of said photoconductor.

27. The method of claim 23, further comprising:
producing an electron hole pair within said photoconductor; and
collecting a charge of said electron hole pair.

28. The method of claim 27, further comprising:
creating a signal based on said collecting;
processing said signal; and
generating an image based on said processing.

29. The method of claim 23, wherein the switching element comprises a thin film transistor.

30. The method of claim 23, wherein the switching element comprises a switching diode.

31. A method for creating one or more X-ray images, comprising:
providing a panel having a first electrode, a second electrode, and a photoconductor secured between said first and second electrodes;
using said photoconductor to absorb X-ray radiation at a first energy level for creating a first image; and
using said photoconductor to absorb X-ray radiation at a second energy level for creating a second image;
wherein each of said first and said second energy levels is a value that is between 10 kilo-electron-volts and 20 Mega-electron-volts, and at least one of said first and said second energy levels is at least 160 kilo-electron volts.

32. The method of claim 31, wherein said photoconductor has a thickness greater than about 1 mm.

33. The method of claim 31, wherein said photoconductor is made from a material selected from the group consisting of Lead Iodide, Cesium Iodide, Mercuric Iodide, Bismuth Iodide, and Cadmium Zinc Telluride.

34. The method of claim 31, wherein said photoconductor comprises a single crystalline layer.

35. The method of claim 31, wherein said photoconductor comprises a poly-crystalline layer.

36. The method of claim 31, wherein said at least one of said first and said second energy levels is higher than 1000 kilo-electron volts.

* * * * *